United States Patent
Kleinwaechter et al.

(10) Patent No.: US 8,724,775 B2
(45) Date of Patent: May 13, 2014

(54) APPLICATOR MEANS FOR X-RAY RADIATION THERAPY, FASTENING MEANS AS WELL AS RADIATION THERAPY DEVICE

(75) Inventors: Timo Kleinwaechter, Muensingen (DE); Frank Weigand, Heidenheim (DE); Frederik Wenz, Heidelberg (DE)

(73) Assignee: Carl Zeiss Meditec AG, Jena (DE)

( * ) Notice: Subject to any disclaimer, the term of this patent is extended or adjusted under 35 U.S.C. 154(b) by 480 days.

(21) Appl. No.: 12/928,793

(22) Filed: Dec. 17, 2010

(65) Prior Publication Data
US 2011/0216885 A1 Sep. 8, 2011

(30) Foreign Application Priority Data
Dec. 17, 2009 (DE) .......................... 10 2009 058 581

(51) Int. Cl.
*A61N 5/10* (2006.01)
*G21K 1/00* (2006.01)

(52) U.S. Cl.
USPC ............................................ 378/65; 378/145

(58) Field of Classification Search
USPC ............................................ 378/64, 65, 145
See application file for complete search history.

(56) References Cited

U.S. PATENT DOCUMENTS

| | | | |
|---|---|---|---|
| 4,266,139 A | 5/1981 | Sportelli et al. | |
| 4,327,293 A | 4/1982 | Taumann | |
| 5,039,867 A | 8/1991 | Nishihara et al. | |
| 5,242,372 A | 9/1993 | Carol | |
| 5,452,720 A | 9/1995 | Smith et al. | |
| 5,947,891 A | 9/1999 | Morrison | |
| 6,048,299 A | 4/2000 | Hoffmann | |
| 6,080,992 A | 6/2000 | Nonaka et al. | |
| 6,159,139 A | 12/2000 | Chiu | |
| 6,421,416 B1* | 7/2002 | Sliski et al. ..................... | 378/65 |
| 7,109,505 B1 | 9/2006 | Sliski et al. | |
| 7,905,822 B2 | 3/2011 | Patrick et al. | |
| 2003/0209677 A1 | 11/2003 | Kumakhov | |
| 2007/0040127 A1 | 2/2007 | Brahme et al. | |
| 2009/0048478 A1 | 2/2009 | Wenz et al. | |
| 2009/0209802 A1 | 8/2009 | Francescatti et al. | |
| 2011/0215260 A1 | 9/2011 | Kleinwaechter et al. | |

FOREIGN PATENT DOCUMENTS

| | | |
|---|---|---|
| CA | 1 097 437 A2 | 3/1981 |
| DE | 44 13 490 C1 | 8/1995 |
| DE | 10 2008 030 590 A1 | 1/2009 |
| EP | 0 259 989 A1 | 3/1988 |
| EP | 1 529 554 A1 | 5/2005 |
| EP | 1 826 778 A2 | 8/2007 |

* cited by examiner

*Primary Examiner* — Irakli Kiknadze
(74) *Attorney, Agent, or Firm* — Kriegsman & Kriegsman (57) ABSTRACT

Among other things, an applicator means (20) for x-ray radiation therapy for the irradiation of surfaces, as well as a radiation therapy device are described, having an applicator element (21) for taking up a probe tip or a radiation source element of a radiation source means (11). In order to further develop applicator means (20) in such a way that it is especially suitable also for the irradiation of surfaces, it is provided that applicator element (21) for adjusting different beam characteristics has at least one element (27) for influencing the beam, in particular a lens element, which is disposed in an exchangeable manner at/in applicator element (21). In addition, an advantageous fastening means is described, by means of which applicator means (20) can be attached and fixed on the surface to be treated.

13 Claims, 12 Drawing Sheets

APPLICATOR MEANS FOR X-RAY RADIATION THERAPY, FASTENING MEANS AS WELL AS RADIATION THERAPY DEVICE

The present invention first of all relates to an applicator means for x-ray radiation therapy according to the preamble of patent claim 1. In addition, the invention also relates to a fastening means for attaching an applicator means according to the preamble of patent claim 9. In addition, the invention also relates to a radiation therapy device.

The present invention, in particular, lies in the field of radiation therapy, and is particularly associated with the irradiation of tumors or the like.

Radiation therapy devices usually are made up of a radiation source means, the operation of which gives rise to radiation, for example, x-ray radiation. The radiation that is generated is guided to the site to be irradiated by means of a probe tip or a radiation source element. For this purpose, so-called applicator means are generally used.

An applicator means, for example, comprises an an applicator element, which is designed for taking up a probe tip or a radiation source element of a radiation therapy device. This means that the probe element or the radiation source element of the radiation therapy device is introduced, for example, inserted, into the applicator element. These types of applicator elements are already known in the prior art.

For example, an applicator means is described in Patent Application DE 10 2008 030 590 A1 of the Applicant, in which the applicator element provides a base body that comprises a number of different regions. A first region is formed by the foot region. It serves for the uptake of at least one component of a radiation therapy device, for example, at least one probe tip or one radiation source element, which represents one component of the radiation therapy device. A largely cylindrical guide region is adjacent to the foot region and this guide region serves for taking up and guiding a probe tip or a radiation source means. A transition region is provided between foot region and guide region. Finally, at its distal end, the applicator provides a head region, where, in particular, the radiation required for an irradiation is released.

In the operation of the radiation therapy device, radiation arises in the probe tip or in the radiation source element, which is released at least in the guide region of the applicator means. Using the applicator means, it can be achieved that body tissue can be directly irradiated at the site of a tumor.

The known applicator means is used in order to make possible an irradiation in very constricted body regions, in particular, in channels or ducts.

Applicator means, however, may also serve for the purpose of irradiating surfaces, for example, the skin or the surfaces of organs.

The object of the present invention is to further develop an applicator means, a fastening means, as well as a radiation therapy device of the type named initially so that they are suitable in a particular way also for the irradiation of surfaces.

This object is achieved according to the invention by the applicator means with the features according to the independent patent claim 1, the fastening means with the features according to the independent patent claim 9, as well as the radiation therapy device with the features according to the independent patent claim 13. Further features and details of the invention can be taken from the subclaims, the description and the drawings. In this case, features and details that are named in connection with the applicator means according to the invention are valid, of course, also in connection with the fastening means according to the invention as well as the radiation therapy device according to the invention, and vice versa correspondingly in each case.

According to the first aspect of the present invention, an applicator means for radiation therapy, in particular for x-ray radiation therapy for the irradiation of surfaces is provided, having an applicator element for taking up a probe tip or a radiation source element of a radiation therapy device. The applicator means is characterized according to the invention in that the applicator element for adjusting different beam characteristics has at least one element for influencing the beam which is disposed in an exchangeable manner at/in the applicator element. In particular, the applicator means is also characterized according to the invention in that the element for influencing the beam is formed as a lens element or as a combination of lens elements.

The irradiation of surfaces in this case particularly involves an irradiation up to a depth of 1 cm or of approximately 1 cm.

An applicator means, which permits and makes possible different beam characteristics by exchanging of at least one element for influencing the beam is thus the foundation of the present invention.

It was previously known in the prior art to produce different beam characteristics in order to irradiate tissue at different depths by having at hand different applicator elements. This was not only complicated, but also expensive. Now, the different beam characteristics can be provided by exchanging the at least one element for influencing the beam. The applicator means as such, however, can also still be utilized, in addition. For this purpose, the element for influencing the beam can be disposed or designed particularly in a detachable manner at/in the applicator element.

The applicator means according to the invention is particularly suitable for the irradiation of the skin or of surfaces of organs, for example, for the surface irradiation of lesions or tumors.

The applicator means may involve, in particular, a surface applicator for radiotherapy.

Basically, the invention is not limited to specific types of elements for influencing the beam, or, however, to a specific number of such elements. Preferably, at least one element for influencing the beam can be designed as a lens element or as a combination of lens elements. The lens element can be designed in one piece or have multiple parts. Several lens elements can be assembled into a combination of lens elements. It is preferably provided that the applicator means having at least one exchangeable lens is equipped for changing the beam characteristic.

Several preferred embodiment examples for the configuration of the lens element or the combination of lens elements are described below.

Preferably, the lens element or the combination of lens elements can be designed as an element or as a combination of elements with a different mass distribution in one plane crosswise to the direction of expansion of the x-ray radiation.

Preferably, the mass distribution of the lens element or the combination of lens elements can be adapted or can be made adaptable to the radiation characteristic of a radiation source means.

The mass distribution is a determining factor for influencing the x-ray radiation. Due to the mass of the element in the radiation path for the x-ray radiation, the radiation is attenuated, whereby a larger mass causes a greater attenuation. The mass distribution in this case can be varied both by the shape as well as also by the selection of materials of the lens element or of the combination of lens elements.

Preferably, the lens element or the combination of lens elements can be designed for generating a radiation characteristic for the applicator means that is independent of the type of radiation source means. For example, a flat or spherical radiation characteristic can be produced in a targeted manner, independently of whether a spherical radiation source or a directed radiation source, such as, for example, a linear accelerator, is used.

For example, the lens element or the combination of lens elements and/or the applicator element—the latter at least in regions—may have a round shape, or a quadrangular shape, or an octagonal shape, or a shape that is adapted to a tumor to be treated.

For example, the lens element or the combination of lens elements may comprise one or at least two different materials.

Preferably, the lens element or the combination of lens elements may have at least one positively curved surface and/or at least one neutral surface and/or at least one negatively curved surface. For example, it may be provided that the two surfaces are identically designed. It is also possible, however, that the surfaces are designed differently from one another. Positively curved surfaces, for example, may be convex surfaces, surfaces with continuous contour, surfaces with a pyramid structure, e.g., a step pyramid structure or the like. Neutral surfaces are, in particular, smooth planar surfaces. Negatively curved surfaces, for example, may be concave surfaces or the like. Various examples of different lens elements are described in connection with FIGS. 5 to 19, and reference is made here also to the full disclosure content thereof. In this case, the embodiment examples that are shown may be produced individually, but also in any desired combination.

In addition, the invention is also not limited to specific embodiments of the applicator means. For example, the applicator means may have an applicator element that first provides a foot region, by means of which the applicator element can be attached to a radiation source means. Thus, the radiation source means and the applicator means can be moved in common. A guide region, particularly a cylindrical guide region, can be connected to the foot region. The guide region, in particular, has an uptake space, into which can be introduced a probe element or a radiation source element of a radiation therapy device. Likewise, the foot region can also have a corresponding uptake space.

In particular, it can be provided that the applicator element is designed as a cylinder, at least in regions.

The applicator element can have a first, free end, which, in particular, opposes a second end. For example, the second end serves for attaching the applicator means to the radiation source means. The first, free end, for example, serves for the purpose of being placed on the surface to be irradiated. In such a case, it can preferably be provided that the element for influencing the beam is provided in the region of the first end of the applicator element.

In the above-named case, the irradiation, or the delivery of radiation, in particular, takes place via the first, free end of the applicator element. That is, the delivery of radiation is made toward the front. Of course, the invention is not limited to this example of embodiment. For example, it can also be provided that the delivery of the radiation takes place in other regions of the applicator element. For example, a lateral irradiation can be provided. Of course, it is also conceivable that the delivery of the radiation is made not only in one region, but in several different regions of the applicator element.

In previously known applicator means, which are used for the irradiation of surfaces, the problem existed that the applicator means usually could be fastened to the surface to be irradiated only in a very complex manner. This problem may also be eliminated with the present invention.

According to a second aspect of the invention, or, however, as another preferred embodiment of the applicator means according to the invention, a fastening means is provided for the attachment onto a surface to be treated of an applicator means for radiation therapy, in particular, for x-ray radiation therapy, particularly for the irradiation of surfaces, which is characterized in that the fastening means has an uptake opening for taking up at least one region of the applicator means.

In this way, the applicator means can be inserted into the uptake opening of the fastening means, for example, by means of its applicator element, in which a probe tip or a radiation source element of a radiation therapy device has been introduced. The fastening means in turn can be attached to the surface to be irradiated.

The fastening means preferably has a base body, which is disposed on or attached to the surface to be treated. In addition, the fastening means has an uptake opening which is formed in a particular way in the base body and, for example, penetrates through it. In such a case, the side walls of the uptake opening that penetrates the base body, at least in regions, serve for supporting and attaching the applicator means in the fastening means.

In this case, the invention is neither limited to specific embodiments of the fastening means, nor to specific possibilities of attachment. Several advantageous, but non-exclusive examples will be explained in more detail in the further course of the description.

The fastening means according to the invention, in particular, is also characterized in that it is formed as a fastening ring.

Preferably, the uptake opening has an inner contour, which corresponds to the outer contour of the region of the applicator means that is to be taken up. Due to the fact that the uptake opening of the fastening means has an inner contour that corresponds to the outer contour of the region of the applicator means to be taken up, it can be assured that the applicator means has a solid seating in the fastening means, which is particularly resistant to slipping out of place. In this case, the invention is not limited to specific embodiments of the uptake opening.

For example, it may be provided that the fastening means has a round uptake opening, and that the round uptake opening has a diameter that corresponds to the outer diameter of a cylindrical applicator means that is to be taken up.

Of course, other embodiments are also conceivable. Thus, the uptake opening can also be designed, for example, quadrangular, preferably square, while the region of the applicator means to be taken up has, for example, a round, cylindrical cross section. The side lengths of the quadrangle may then preferably correspond to the diameter of the round segment, so that the applicator means can be securely attached and fixed in the uptake opening and thus in the fastening means. Of course, other geometries are also conceivable. It is only important that the applicator means can be introduced into the uptake opening of the fastening means and can be held therein.

If the irradiation or the delivery will take place toward the front, i.e., via the first, free end of the applicator element, the fastening means is preferably designed, for example, as a fastening ring, in the above-named way. If an irradiation or the delivery of the radiation is to take place via other regions of the applicator element, for example, laterally, the fastening means can be designed in suitable ways, which makes possible a lateral delivery of the radiation. For example, the fastening means could be made L-shaped in such a case.

The fastening means is fastened onto the surface to be treated. This can be accomplished in different ways.

For example, it may be provided that the fastening means can be attached and fixed directly onto the surface to be irradiated, for example, with double-sided adhesive tape.

Preferably, it can be provided that the fastening means has at least one outwardly projecting fastening tab on at least one of its outer sides. Of course, several such fastening tabs may also be provided. With the presence of such fastening tabs, it can be provided, for example, that these can be attached and fixed onto the surface to be irradiated with normal adhesive tape.

Preferably, at least one fastening tab can have at least one fastening opening. In this way, it is made possible, in particular, that the fastening means can also be sewn in order to fix it in place. This may be of advantage, for example, in the irradiation of organs.

According to a third aspect of the invention, a radiation therapy device is provided with a radiation source means, in particular for x-ray irradiation, particularly for irradiation of surfaces The radiation therapy device has an applicator means for taking up a probe tip or a radiation source element of the radiation source means, whereby the applicator means is designed in the above-described way according to the invention, so that in this respect, reference is made to the full content of the above statements relating to the applicator means. Alternatively or additionally, the radiation therapy device may have a fastening means according to the invention, as described above, for fastening an applicator means for radiation therapy onto a surface to be treated, so that, in this respect also, reference is made to the full content of the above statements relating to the fastening means.

The radiation therapy device may be used particularly for the irradiation of surfaces, for example, for the irradiation of the skin or of the surface of an organ.

The radiation therapy device first has a radiation source means, by means of which the radiation doses necessary for the irradiation will be produced. In particular, the radiation source means is designed for generating radiation for radiotherapy. The applicator means is disposed at the radiation source means.

The invention will now be explained in more detail on the basis of embodiment examples with reference to the appended drawings. Here.

Figure 1:
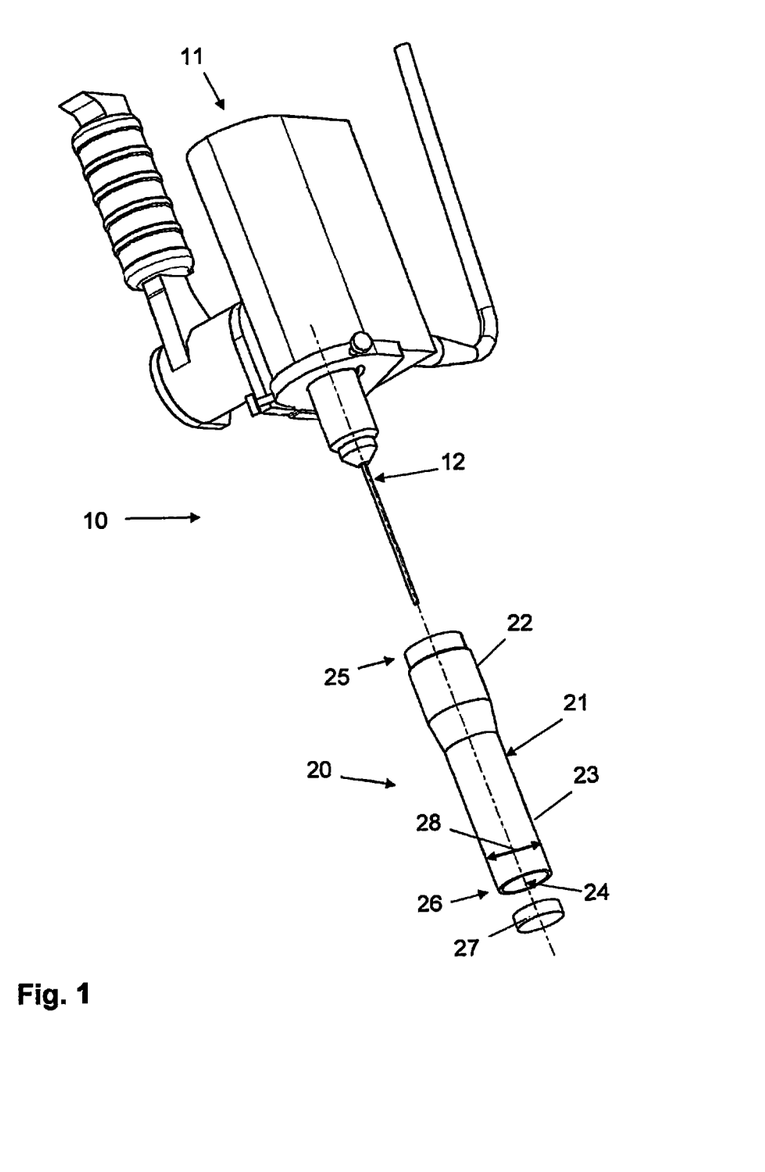
FIG. 1 is a perspective representation of individual components of the radiation therapy device according to the invention having the applicator means according to the invention.
Figure 2:
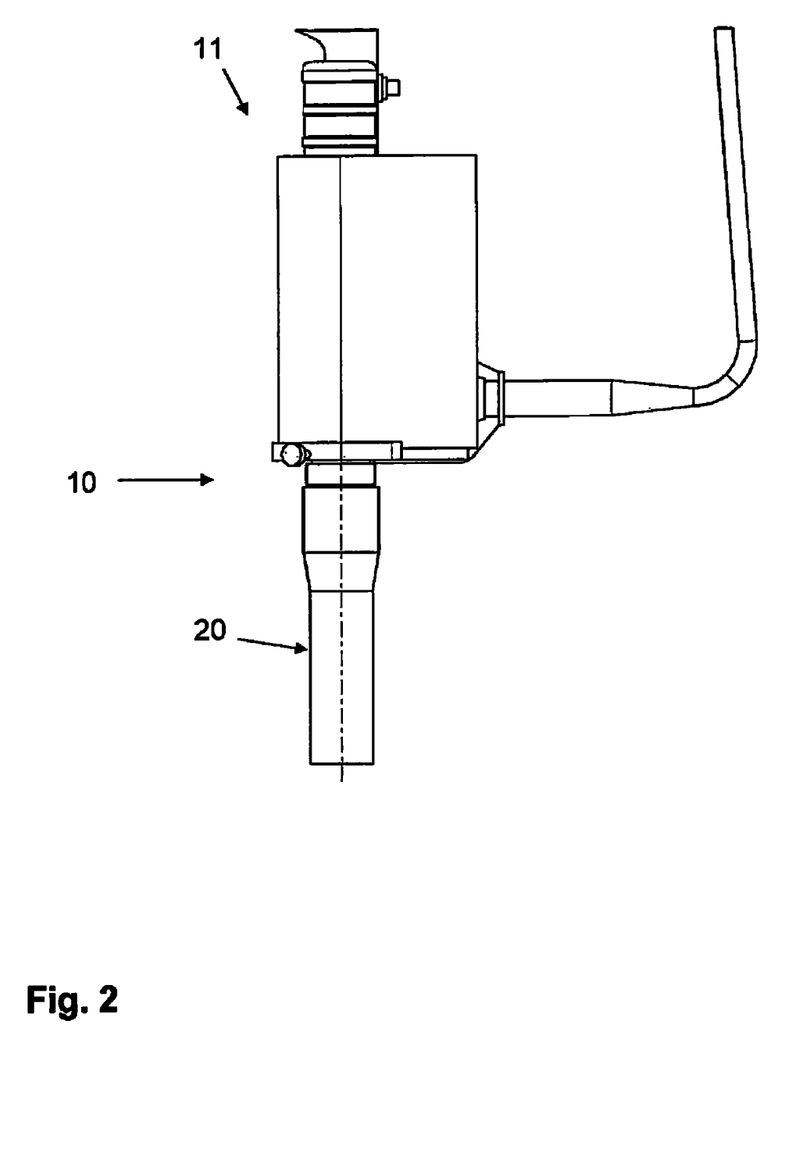
FIG. 2 is a representation of the radiation therapy device according to FIG. 1 in the assembled state.
Figure 3:
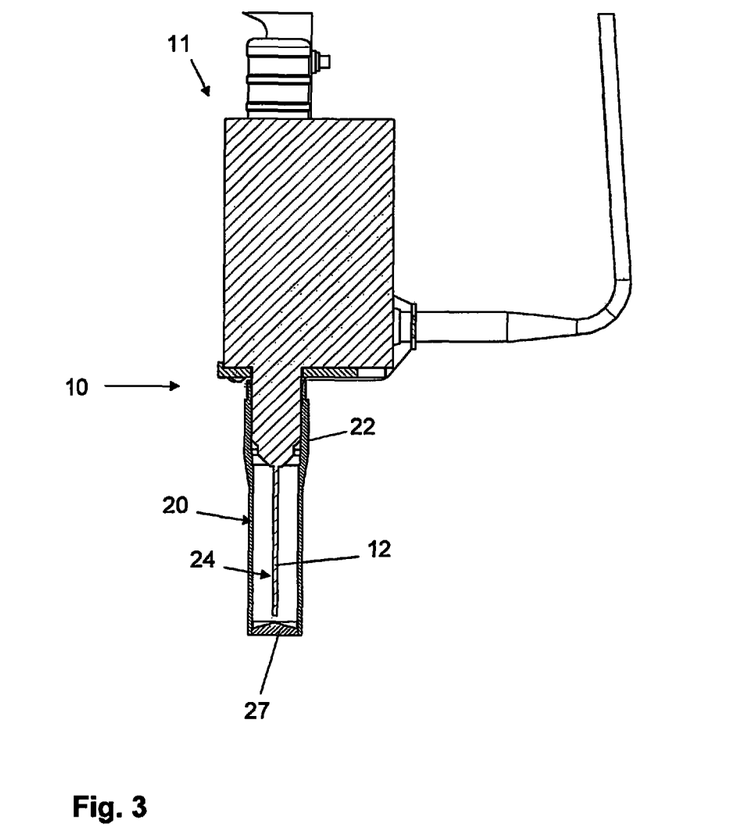
FIG. 3 is a cross-sectional view of the radiation therapy device according to the invention according to FIG. 2.

A radiation therapy device 10 is shown in FIGS. 1 to 3. Radiation therapy device 10 has a radiation source means 11, which is designed for generating radiation for radiotherapy. A radiation source element 12 is provided for applying the generated radiation. Radiation therapy device 10 serves for x-ray radiation therapy.

As is shown further in FIGS. 1 to 3, an applicator means 20 according to the invention has a cylindrically shaped applicator element 21. Applicator element 21 comprises a foot region 22 and a guide region 23 connecting thereto. In particular, the radiation source element 12 of radiation source means 11 of radiation therapy device 10 is found in irradiation operation, as is illustrated particularly also in FIG. 3. For this purpose, guide region 23 of applicator element 21 has a corresponding uptake space 24.

Applicator element 21 has a second end 25 in foot region 22, by means of which applicator element 21, and thus applicator means 20, can be attached to radiation source means 11. The first end 26 of applicator element 21, which lies opposite to the second end 25, involves the free end of applicator element 21, which terminates the guide region 23 of applicator element 21, and the radiation dose can be applied by first end 26, for example, onto the surface to be irradiated.

In order to be able to generate different beam characteristics with applicator means 20, for example, in order to be able to irradiate a tissue to be irradiated at different depths, applicator means 20 has an element 27 for influencing the beam in the example of embodiment shown in FIGS. 1 to 3. Element 27 for influencing the beam is advantageously designed as a lens 27 for changing the beam characteristic. It is preferably exchangeable, i.e., detachably disposed on applicator element 21, preferably in the region of its first free end 26.

In FIG. 2, the radiation therapy device 10 according to FIG. 1 is shown in a state in which applicator means 20 and radiation therapy device 10 are assembled. FIG. 3 shows a cross-sectional view of the radiation therapy device 10, which is assembled as shown in FIG. 2.

In particular, FIG. 3 shows how applicator means 20 is attached via its foot region 22 to radiation source means 11. Radiation source means 11 and applicator means 20 form components of radiation therapy device 10. Radiation, for example, radiation for radiotherapy is produced in radiation source means 11 and is applied onto the surface to be irradiated via radiation source element 12, which is connected to radiation source means 11 and which is found in uptake space 24 inside applicator element 21.

In particular, if a surface is to be irradiated, it is often difficult to configure applicator means 20 so that it can be attached to the site that is to be irradiated. In order to eliminate this problem, a special fastening means 30 is provided, which is described in more detail below in connection with FIG. 4.

Figure 4:
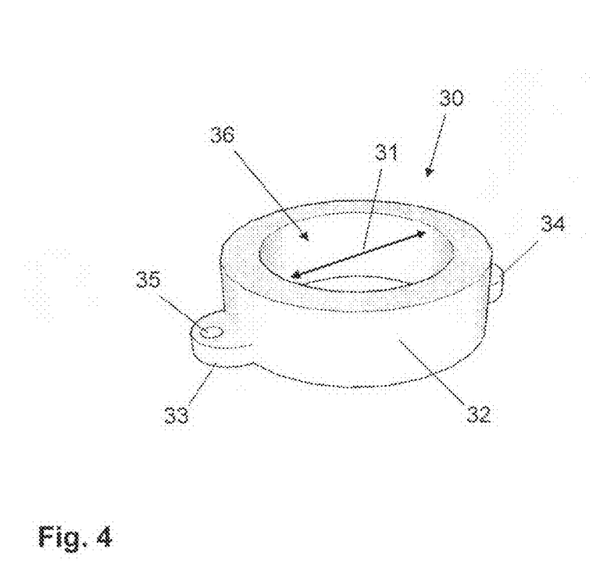
FIG. 4 is a representation of a fastening means for attaching an applicator means.

Fastening means 30 is designed as a fastening ring, by means of which the applicator means 20 can be attached and fixed onto the surface to be treated. Fastening ring 31 has an uptake opening 36 for applicator element 21, whereby uptake opening 36 has an inner diameter 31, which corresponds to outer diameter 28 of applicator element 21 in the region of its first end 26, as this is also illustrated in FIGS. 1 and 3. In this way, applicator means 20 can be inserted into fastening ring 30 and can be held therein so that it cannot slip out of position.

Fastening ring 30, in turn, can be attached and fixed onto the surface to be treated, for example, the skin, e.g., with the use of double-sided adhesive tape. Alternatively, it can be provided that fastening ring 30 has at least one fastening tab projecting outwardly from its outer side 32. Two such fastening tabs 33, 34 are shown in FIG. 4, whereby the number may vary according to the application. In such a case, fastening ring 30 can be attached and fixed via fastening tabs 33, 34 onto the surface to be treated also with normal adhesive tape. If fastening openings 35 are found in fastening tabs 33, 34, fastening ring 30 can also be solidly sewn in place for attachment, for example. This may be of advantage, for example, in the irradiation of organs.

On the basis of FIGS. 5 to 19, different embodiment examples of elements 27 for influencing the beam are shown, which can be used in an applicator means 20 as described above. Elements 27 involve lens elements. A lens element in the sense of the Patent Application in this case is, in particular, an element with a different mass distribution in a plane crosswise to the expansion direction of the x-ray radiation. The mass distribution of lens element 27 is thus ideally adapted to the radiation characteristic of radiation source means 11. The mass distribution is a determining factor for influencing the x-ray radiation. Due to the mass of lens element 27 in the beam path of the x-ray radiation, the radiation is attenuated, whereby a larger mass causes a greater attenuation. The mass distribution in this case can be varied both by the shape as well as also by the selection of materials of lens element 27.

In this way, a radiation characteristic of applicator means 20 that is independent of the type of radiation source means 11 can be adapted.

In the following, different embodiment examples for lens elements 27 with different mass distributions are described, which can be used for applicator means 20 shown in FIGS. 1 to 3.

Figure 5:
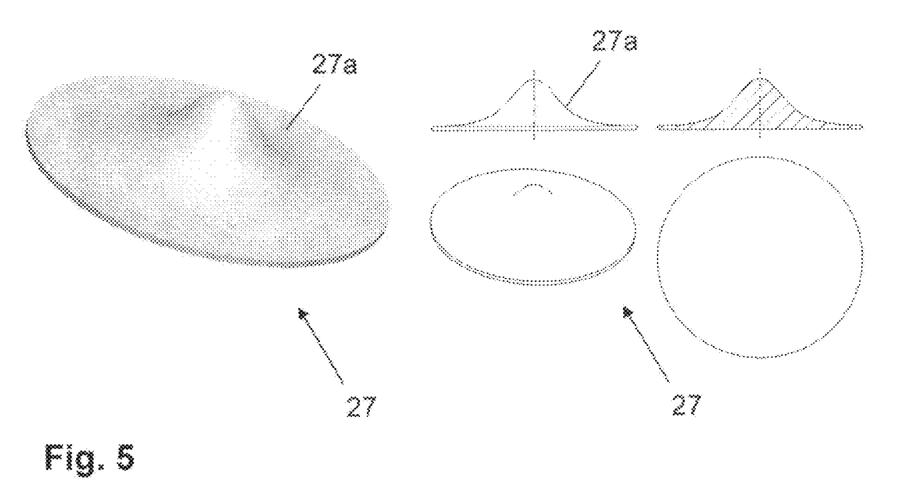
FIGS. 5 to 19 are various embodiment examples of elements for influencing the beam, which may be used in a radiation therapy device according to FIGS. 1 to 3.

FIG. 5 shows an element 27 for influencing the beam in the form of a lens element that comprises one material and has a round shape. One surface 27a of lens element 27 in this case has a positive curvature in the form of a continuous contour.

Figure 6:
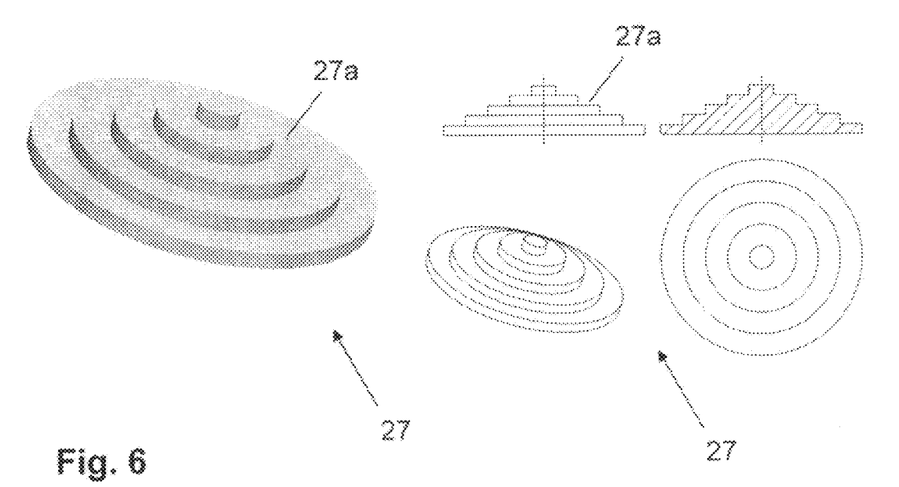
Figure 7:
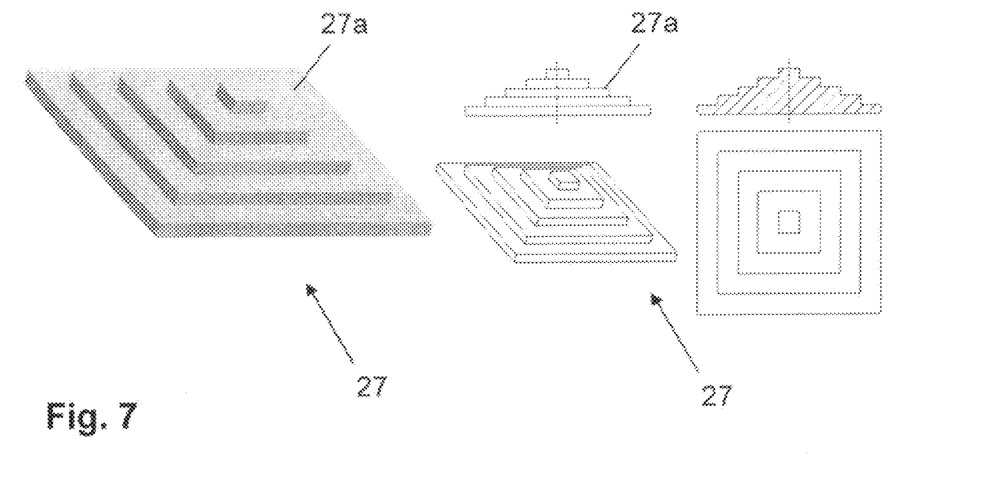

FIG. 6 shows an element 27 for influencing the beam in the form of a lens element that comprises one material and has a round shape. One surface 27a of lens element 27 in this case has a positive curvature in the form of a contour in the shape of a step pyramid. The individual steps of the step pyramid in this case could also comprise different materials, at least in part. FIG. 7 shows a similar example of embodiment, except that the lens element has a quadrangular shape.

Figure 8:
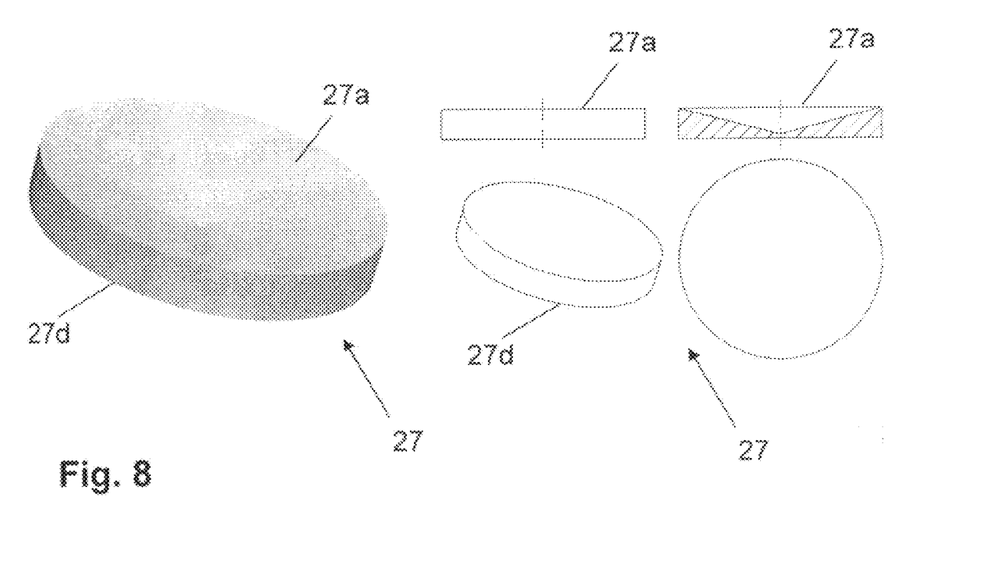
Figure 9:
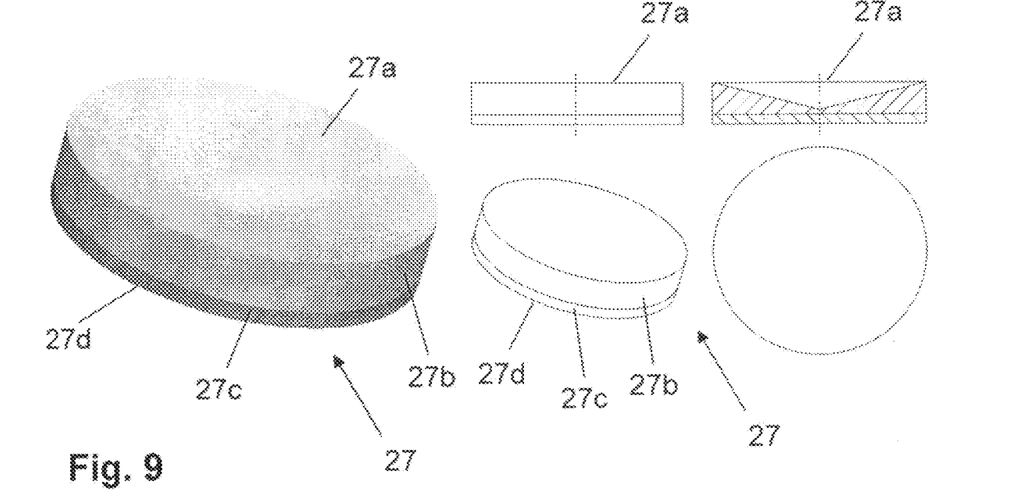
Figure 10:
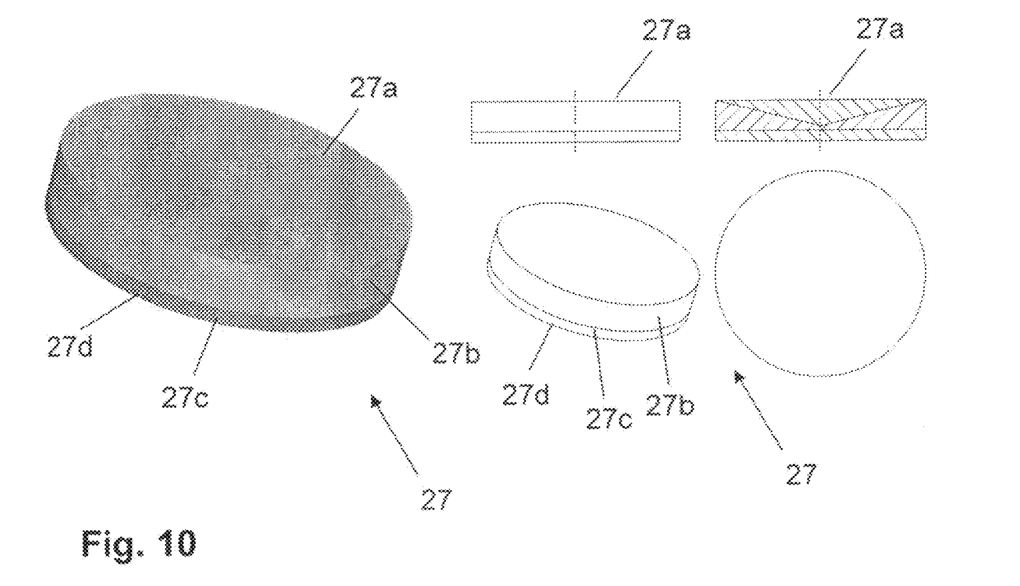

FIG. 8 shows an element 27 for influencing the beam in the form of a lens element that comprises one material and has a round shape. One surface 27a of lens element 27 in this case has a negative curvature in the form of a concave contour. The other surface 27d has a neutral, smooth contour. The depicted element involves a focus element. FIG. 9 shows a similar example of embodiment, except that the element comprises two different materials 27b, 27c. The example of embodiment shown in FIG. 10 is similar to the example of embodiment shown in FIG. 9, whereby the surface is designed as neutral in the form of a smooth surface. This can be produced, for example, by means of a refilling.

Figure 11:
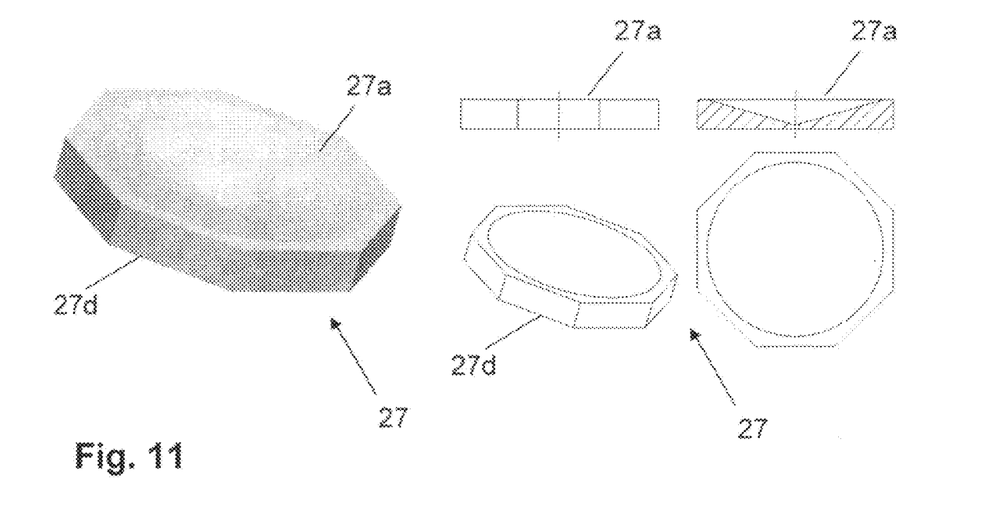
Figure 12:
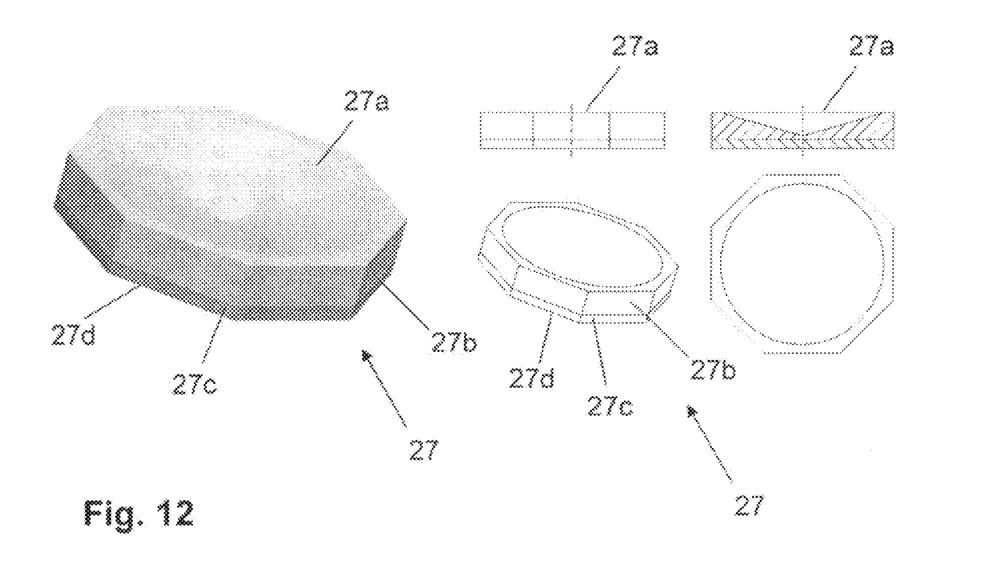

FIG. 11 shows an element 27 for influencing the beam in the form of a lens element that comprises one material and has an octagonal shape. One surface 27a of lens element 27 in this case has a negative curvature in the form of a concave contour. The other surface 27d has a neutral, smooth contour. The depicted element involves a focus element. FIG. 12 shows a similar example of embodiment, except that the element comprises two different materials 27b, 27c.

Figure 13:
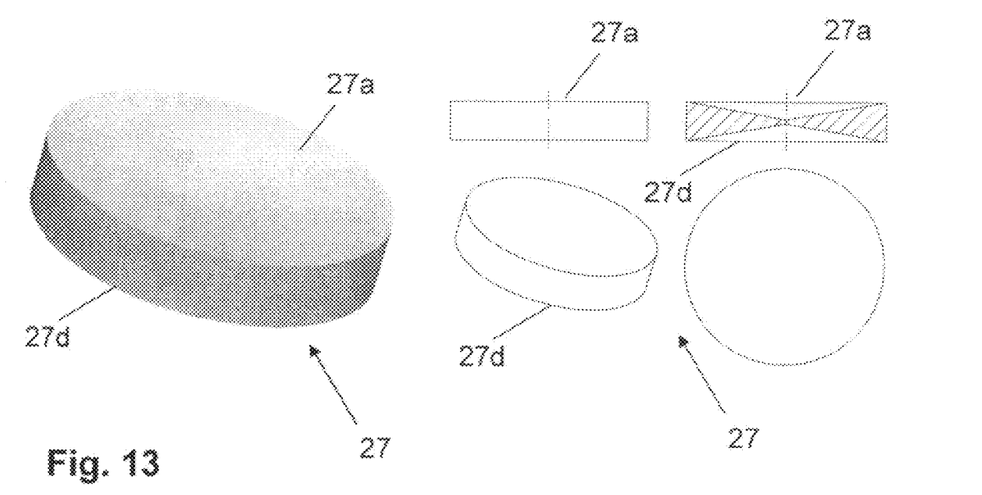

FIG. 13 shows an element 27 for influencing the beam in the form of a lens element that comprises one material and has a round shape. Both surfaces 27a, 27d of lens element 27 in this case have a negative curvature in the form of a concave contour. The depicted element involves a focus element.

Figure 14:
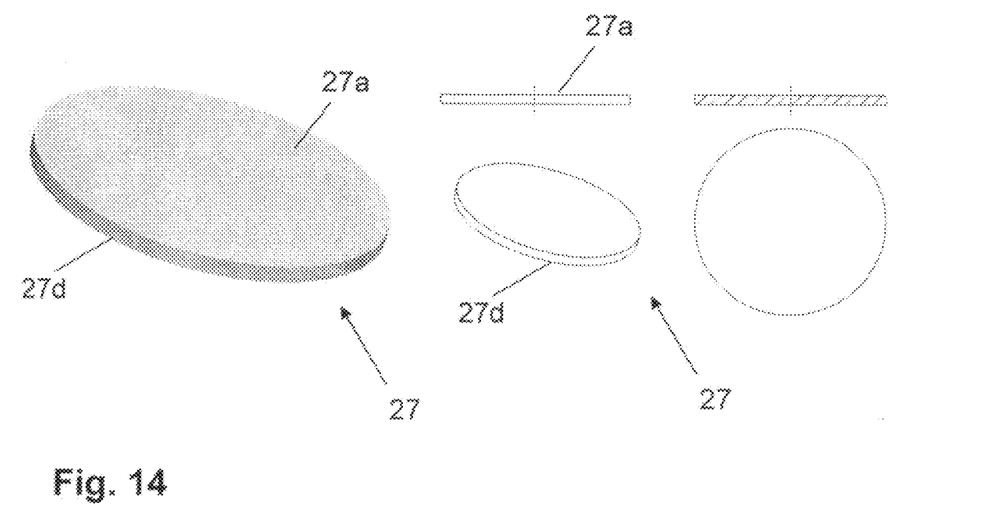

FIG. 14 shows an element 27 for influencing the beam in the form of a lens element that comprises one material and has a round, flat shape. Both surfaces 27a, 27d of lens element 27 in this case have a neutral, smooth contour.

Figure 15:
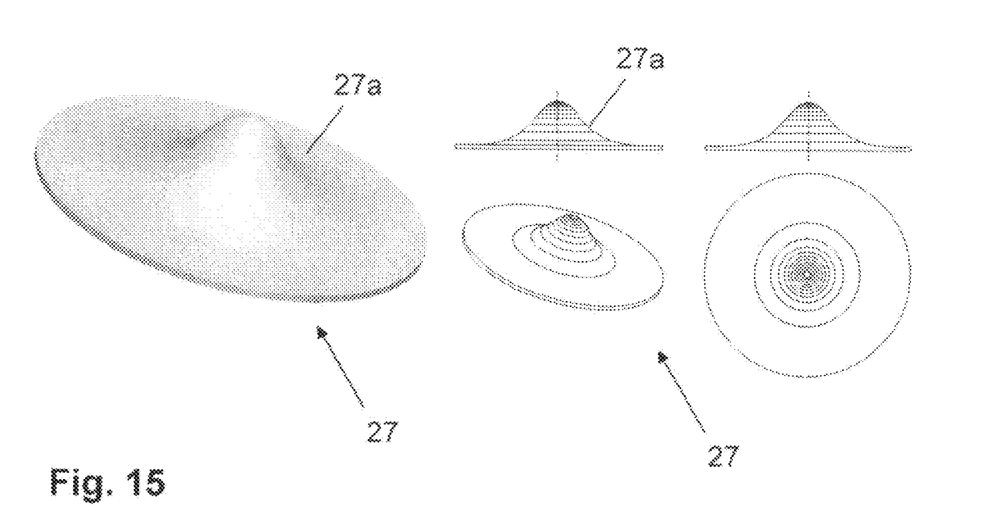

FIG. 15 shows an element 27 for influencing the beam in the form of a lens element that has a round shape. One surface 27a of lens element 27 in this case has a positive curvature in the form of a continuous contour. Element 27 comprises several materials. In the example of embodiment shown, element 27 comprises materials with decreasing density.

Figure 16:
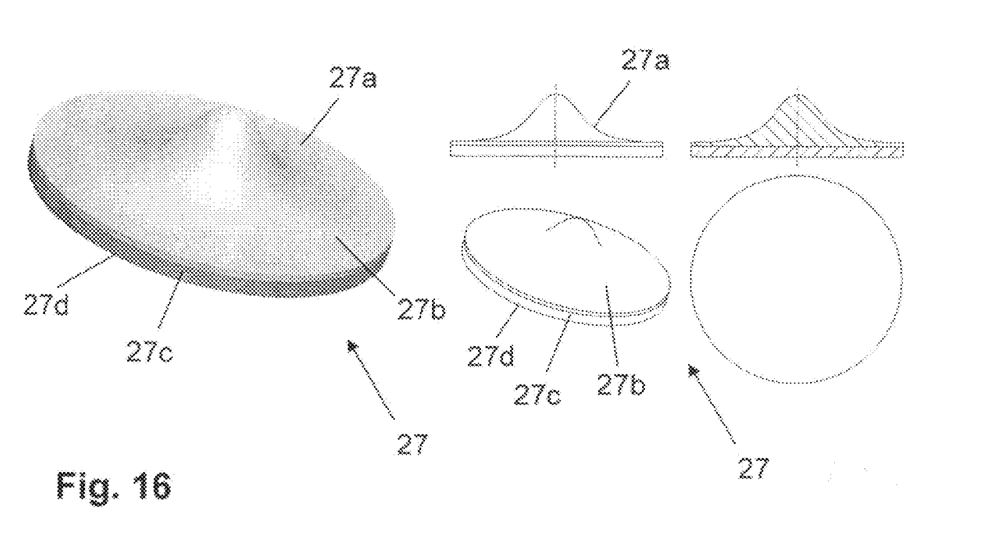

FIG. 16 shows an element 27 for influencing the beam in the form of a lens element that has a round shape. One surface 27a of lens element 27 in this case has a positive curvature in the form of a continuous contour. The other surface 27d has a neutral, smooth contour. Element 27 comprises several materials 27b, 27c.

Figure 17:
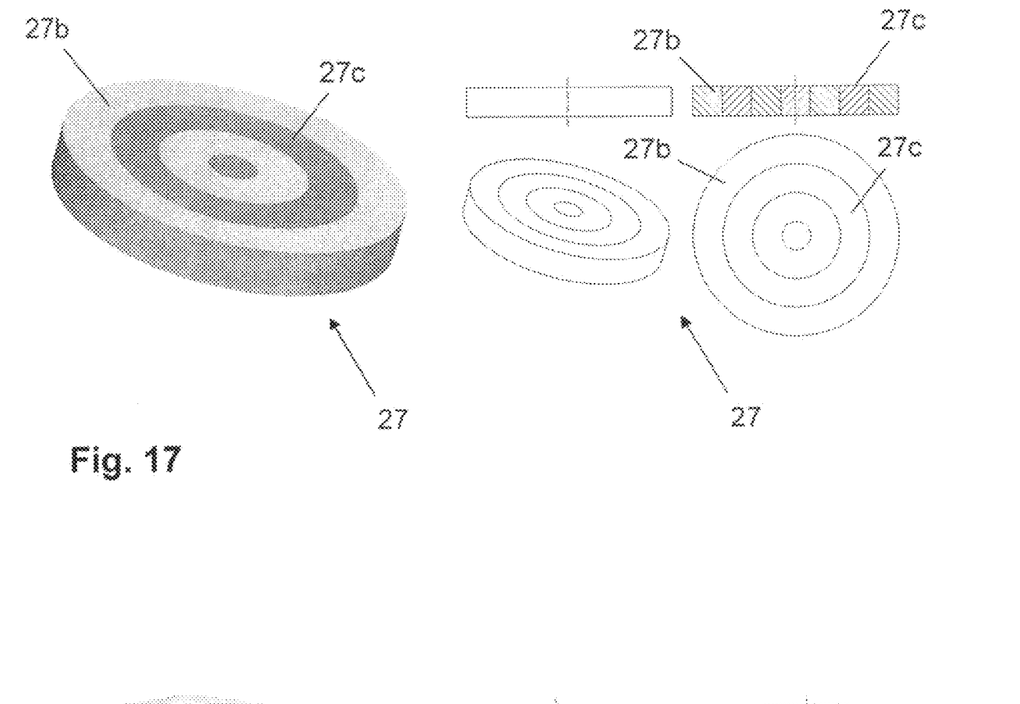

FIG. 17 shows another example of embodiment for an element 27 for influencing the beam in the form of a lens element that comprises two different materials 27b, 27c. In this case, element 27 is designed as a ring.

Figure 18:
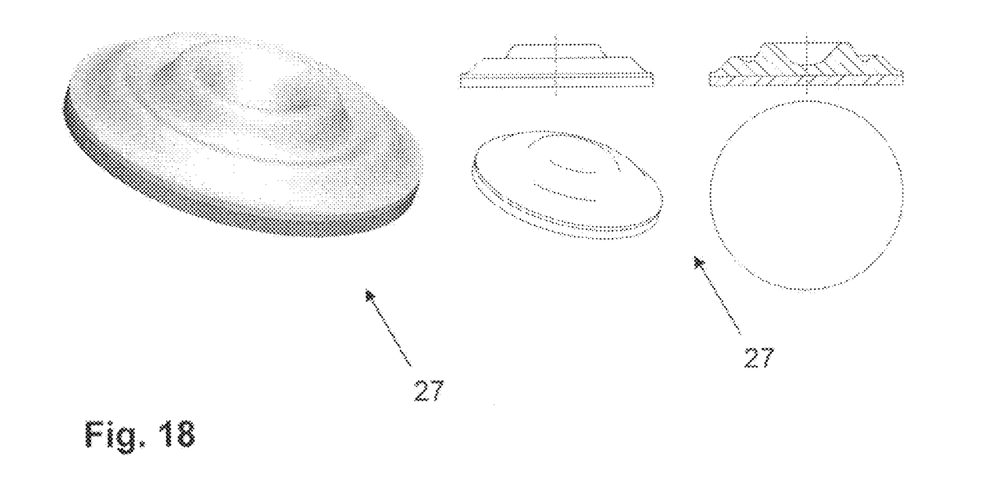

FIG. 18 shows yet another example of embodiment of an element 27 for influencing the beam in the form of a lens element with an unusual shape.

Figure 19:
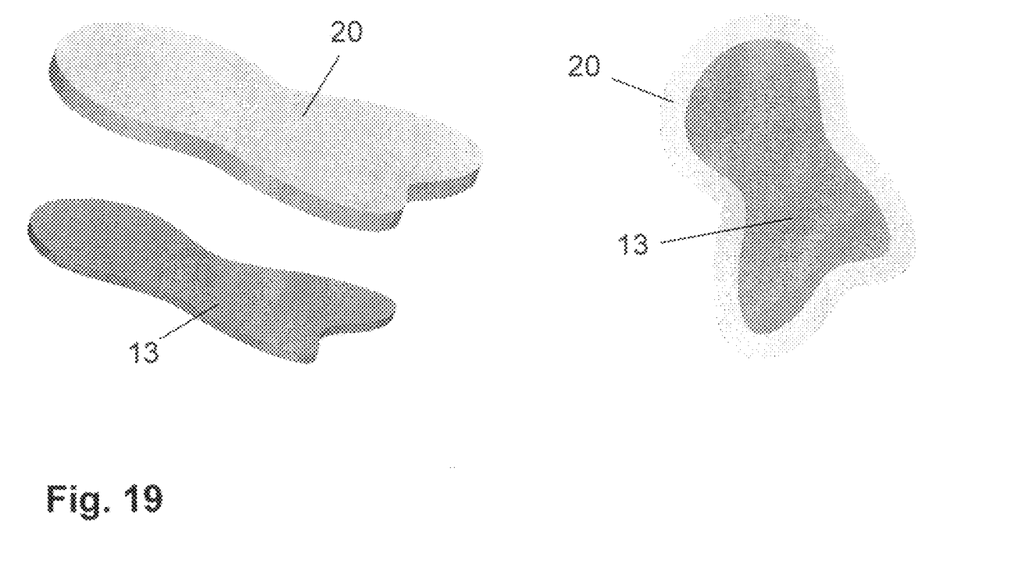

Finally, in FIG. 19, an example of embodiment is shown, in which applicator means 20, and alternatively or additionally, element 27 for influencing the beam is/are adapted to the shape of a tumor 13 to be treated.

The embodiment examples described above and shown in the Figures are particularly suitable for the irradiation of surface lesions or tumors, in particular on the skin or on the surface of organs.

LIST OF REFERENCE SYMBOLS

10 Radiation therapy device
11 Radiation source means
12 Radiation source element
13 Tumor
20 Applicator means
21 Applicator element
22 Foot region
23 Guide region
24 Uptake space
25 Second end of the applicator element
26 First end of the applicator element
27 Element for influencing the beam (lens element)
27a Surface
27b Material
27c Material
27d Surface
28 Outer diameter
30 Fastening means (fastening ring)
31 Inner diameter
32 Outer side
33 Fastening tab
34 Fastening tab
35 Fastening opening
36 Uptake opening

The invention claimed is:

1. An applicator means for x-ray radiation therapy for the irradiation of surfaces, having an applicator element for taking up a probe tip or a radiation source element of a radiation source means, is hereby characterized in that the applicator element for adjusting different beam characteristics has at least one element for influencing the beam, which is disposed in an exchangeable manner at/in the applicator element, that the element for influencing the beam is designed as a lens element or as a combination of lens elements, and that the lens element or the combination of lens elements is designed as an element or a combination of elements with a different mass distribution in one plane crosswise to the direction of expansion of the x-ray radiation.

2. The applicator means according to claim 1, further characterized in that the mass distribution of the lens element or of the combination of lens elements is adapted or is adaptable to the radiation characteristic of a radiation source means.

3. The applicator means according to claim 1, further characterized in that the lens element or the combination of lens elements and/or the applicator element has a round, or quadrangular, or octagonal shape, or has a shape adapted to a tumor.

4. The applicator means according to claim 1, further characterized in that the lens element or the combination of lens elements comprises one material or at least two different materials.

5. The applicator means according to claim 1, further characterized in that the lens element or the combination of lens elements has at least one positively curved surface and/or at least one neutral surface and/or at least one negatively curved surface.

6. The applicator means according to claim 1, further characterized in that the applicator element has a first end for positioning on the surface to be irradiated, and that element for influencing the beam is provided in the region of the first end of applicator element.

7. The applicator means according to claim 1, further characterized in that applicator element is designed as a cylinder, at least in regions.

8. A fastening means for fastening an applicator means for x-ray radiation therapy for the irradiation of surfaces, in particular, an applicator means according to claim 1, onto a surface to be treated, is characterized in that the fastening means has an uptake opening for taking up at least one region of applicator means, and that fastening means is designed as a fastening ring.

9. The fastening means according to claim 8, further characterized in that uptake opening has an inner contour, which corresponds to the outer contour of the region of applicator means that is to be taken up.

10. The fastening means according to claim 8, further characterized in that fastening means has at least one outwardly projecting fastening tab on at least one outer side.

11. The fastening means according to claim 10, further characterized in that at least one fastening tab has at least one fastening opening.

12. A radiation therapy device for the x-ray irradiation of surfaces, having a radiation source means and having an applicator means for taking up a probe tip or a radiation source element of the radiation source means, wherein the applicator element for adjusting different beam characteristics has at least one element for influencing the beam, which is disposed in an exchangeable manner at/in the applicator element, that the element for influencing the beam is designed as a lens element or as a combination of lens elements, and that the lens element or the combination of lens elements is designed as an element or a combination of elements with a different mass distribution in one plane crosswise to the direction of expansion of the x-ray radiation and/or having a fastening means according to claim 8 for attaching an applicator means for x-ray radiation therapy onto a surface to be treated.

13. The applicator means according to claim 1, further characterized in that the lens element or the combination of lens elements has a plane surface at its outer face.

\* \* \* \* \*